United States Patent [19]

Bond

[11] 4,445,899
[45] May 1, 1984

[54] HYGIENIC ARTICLE FOR BLOTTING THE RECTAL PERINEUM REGION

[76] Inventor: Helen I. Bond, 709 Olson Rd., Longview, Wash. 98632

[21] Appl. No.: 341,304

[22] Filed: Jan. 21, 1982

[51] Int. Cl.$^3$ .............................................. A61B 19/00
[52] U.S. Cl. .................................... 604/385; 604/286; 604/374; 604/378; 604/904
[58] Field of Search ............... 604/358, 367, 374, 377, 604/378, 380, 379, 384, 385, 904; 128/1 R

[56] References Cited

U.S. PATENT DOCUMENTS

| | | | |
|---|---|---|---|
| Re. 28,674 | 1/1976 | Guyette | 604/377 X |
| 3,570,489 | 3/1971 | Brown | 604/904 X |
| 3,572,341 | 3/1971 | Glassman | 604/380 X |
| 3,946,737 | 3/1976 | Kobler | 604/904 X |
| 4,018,225 | 4/1977 | Elmi | 604/374 X |
| 4,209,009 | 6/1980 | Hennig | 128/1 R |
| 4,211,225 | 7/1980 | Sibalis | 604/904 X |
| 4,212,301 | 7/1980 | Johnson | 604/904 X |
| 4,335,721 | 6/1982 | Matthews | 604/904 X |

FOREIGN PATENT DOCUMENTS 1791259  2/1973  Fed. Rep. of Germany ...... 604/904

Primary Examiner—C. Fred Rosenbaum
Assistant Examiner—Michelle N. Lester
Attorney, Agent, or Firm—George R. Nimmer

[57] ABSTRACT

Disclosed are hygienic articles for the rectal perineum region and comprising a blotter member formed of hydrophilic fibers and including: a nodular button of compressed fibers emplaceable within a flaccid anus; a wick of looser fibers located immediately above the anus-emplaced nodular button whereas to absorb rectal secretia and convey same toward the emplaced nodular button; and a relatively massive and lengthy flap of fibers extending downwardly from the nodular button and communicating with the wick. A flexible skirt member might surround the blotter member flap immediately below the nodular button and conform as two folds against the two perineal walls. Therapeutic and/or drying agents might be impregnated into the blotter and/or skirt members.

11 Claims, 8 Drawing Figures

HYGIENIC ARTICLE FOR BLOTTING THE RECTAL PERINEUM REGION

Hemorrhoids or other anatomical abnormality can cause flaccidity of the anus muscular structure whereby the victim is plagued with the involuntary discharge of rectal secretia from the anus which causes fouling and irritation of the perineal walls and soiling of the undergarments. Very frequent aqueous bathing is effective, but time-consuming and oftentimes not available. Accordingly, sufferers of anus flaccidity have attempted to stem the involuntary discharge of rectal secretia by the usage of hydrophilic fibers positioned immediately below the anus between the perineal walls. Hydrophilic fibers in the form of wadded cellulosic paper e.g. facial or bathroom tissue, might be pressed into the buttocks cleavage, but such is apt to become dislodged whenever the user is walking about. Though hydrophilic fibers in the form of cylindrical catamenial tampons might be partially emplanted within the anus, their diameter overextends the anus and moreover causes extreme discomfort and chafing to the perineal walls.

It is accordingly the general objective of the present invention to provide hygienic articles for use at the rectal perineum region and that will controllably convey discharge of rectal secretia from a flaccid anus, that will remain reliably positioned within the anus while the user is walking about, that can be readily replaced after use with a substitute like article, that does not require sanitary-belts or other fastener means, that does not cause discomfort to the anus nor to the perineal walls, and that protects and even possibly affirmatively treats the perineal walls.

With the above and other objects and advantages in view, which will become more apparent as this description proceeds, the hygienic article for the rectal perineum region generally comprises a blotter member including a bundle portion of coherent hydrophilic fibers and a nodular button portion so as to divide the bundle at a constriction into a relatively short length wick and a relatively lengthy and more massive tuft-like flap, the nodular button comprising relatively highly compressed hydrophilic fibers and being emplaceable within the anus so as to retard the rectal secretia being conveyed downwardly by the upper wick, the bundle portion flap being nestably positionable immediately below the anus so as to conformably abut against the user's perineal walls, and together with flexible skirt member and other optionally employable features which will be explained in detail as this description proceeds.

In the drawing, wherein like characters refer to like parts in the several views, and in which.

Figure 2:
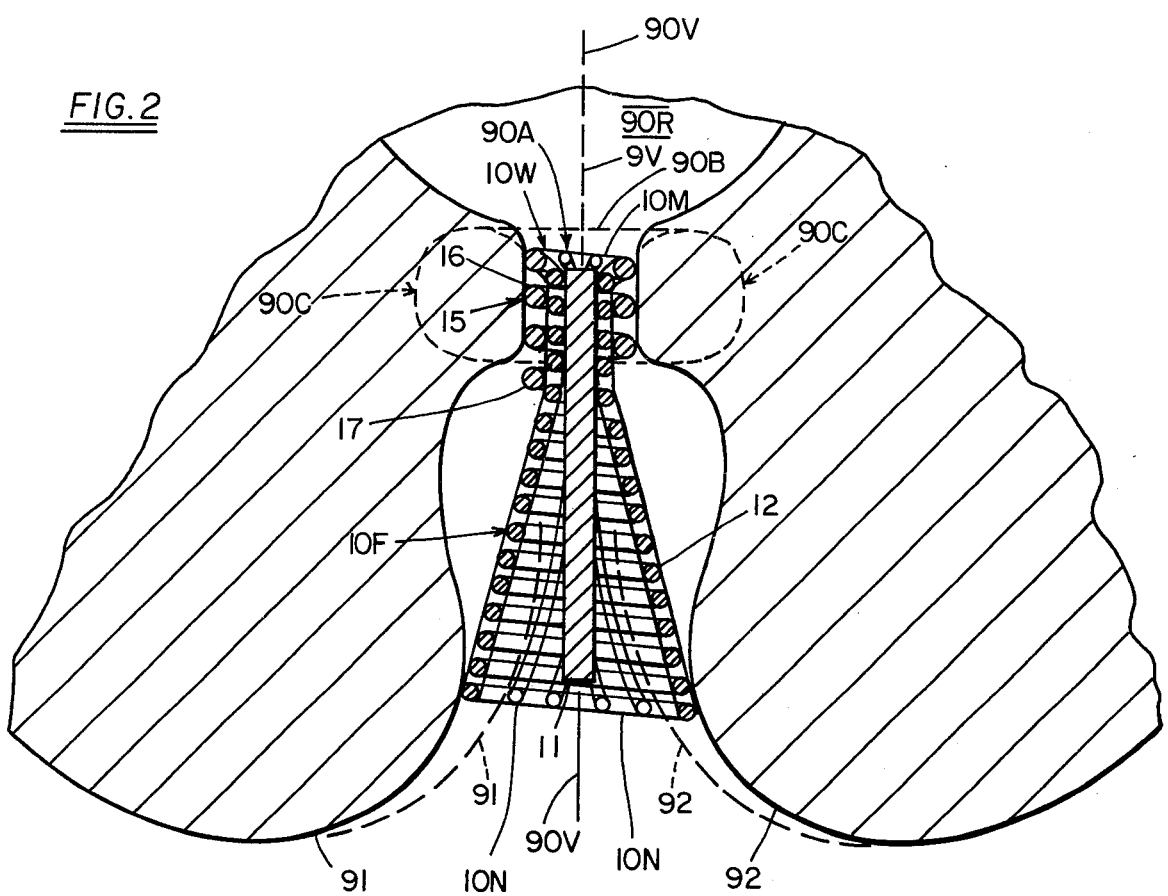
FIG. 2 is a sectional elevational view taken along line 2—2 of FIG. 1 and shown removably emplaced at the rectal perineum anatomical region.
Figure 1:
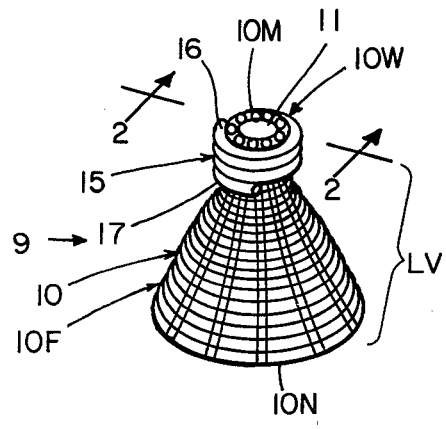
FIG. 1 is a perspective view of a representative first embodiment of the hygienic article for the perineum region of the present invention.

Turning initially to drawing FIGS. 1 and 2 which depict first embodiment 9 of the hygienic article concept of the present invention. Representative embodiment 9 comprises a blotter member comprising a bundle 10 of coherent hydrophilic fibers extending for a longitudinal-length "LV" along article central-axis 9V, from bundle lead-end 10M to bundle trail-end 10N, said blotter member also comprising a nodular button 15 constrictably surrounding bundle 10 and delineating the juncture of bundle 10 into a wick (10W) and a flap (10F). In embodiment 9, bundle 10 comprises two longitudinally coextensive (10M-10N) parts including a central core 11 of hydrophilic fibers extending along central-axis 9V and a woven gauze wrap 12 of further hydrophilic fibers surrounding central-axis 9V and fibrous core 11. Nodular button 15 has an upper extremity 16 and a lower extremity 17, and these two extremities are so located with respect to each other and to bundle ends 10M and 10N that:

a. the bundle wick length (10M-16) is relatively short and on the order of about one-fourth inch;

b. the bundle flap length (17-10N) bears a manyfold ratio compared to the wick length (10M-16), and the bundle flap 10F is at least ten-fold more massive than the shorter wick part 10W; and c. the longitudinal length from button lower extremity 17 to bundle lead-end 10M need not exceed about one-half inch. The nodular button 15 comprises hydrophilic fibers compressed more closely together than are the fibers of bundle 10; in embodiment 9, nodular button 15 comprises a strand of entwined hydrophilic fibers wrapped tightly around the blotter member bundle portion 10. Both the bundle and the nodular button portions are preferably devoid of inorganic acidic or alkaline materials. Another variation of the first embodiment might include a wrap comprising a numerous plurality of vertical strings tightly surrounded by a nodular button (e.g. 15).

FIG. 2 shows embodiment 9 in the anatomical environment at rectum 90R extending along rectal-axis 90V and having its lower terminus at the top-end 90B of anus 90A which surrounds rectal-axis 90V. The anal sphincter muscle 90C is depicted in phantom line, and the perineal walls 91 and 92 are depicted in solid line though in phantom line when in flexure against compressible flap 10F. The hygienic article 9 at nodular button 15 is removably emplaceable within anus 90A and surrounded by sphincter muscle 90C as to removably maintain article 9 thereat. Bundle wick 10W is thereby positionable within the confines of muscle 90C so that lead-end 10M does not extend substantially upwardly beyond anus top-end 90B. Concommitantly, bundle flap 10F is nestably locatable immediately below anus 90A so as to conformably abut against the perineal walls 91 and 92. Thus, bundle wick 10W absorbs rectal secretia and conveys same along the bundle fibers (e.g.

11, 12) toward bundle flap 10F. However, nodular button 15 acts as a retarder which desireably slows the rectal secretia being conveyed along colinear axes 9V and 90V from wick 10W toward flap 10F and thereby reduce irritation and promote cleanliness at the perineal walls. In the latter regard, bundle flap 10F might have a therapeutic or drying agent impregnated therewithin. The bundle flap (e.g. 12), converging toward the lower extremity of the nodular button constriction, might sheath the operator's index finger ancillary to removably emplacing the hygienic article within the anus 90A.

Figure 3:
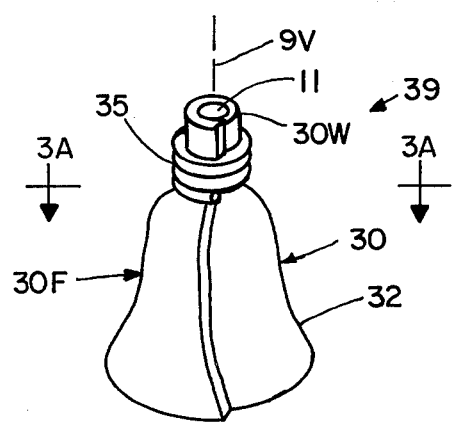
FIG. 3 is a perspective view similar to FIG. 1 showing a second embodiment of the hygienic article of the present invention.
Figure 3A:
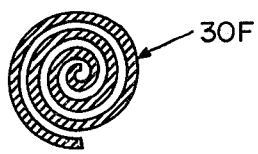
FIG. 3A is a fragmentary view taken along the line 3A—3A of FIG. 3.

Second embodiment 39 of FIGS. 3 and 3A has a bundle 30, which, instead of the core 11 and the woven gauze wrap 12, comprises a single length of sheet material of sheet-oriented randomly disposed hydrophilic fibers, which sheet is convolutely wound around central-axis 9V. As is readily apparent from the FIG. 3A sectional plan view, the sheet convolutions become progressively closer to central-axis 9V, as might be provided by a progressively looser winding about a removable longitudinal mandrel.

Figure 4:
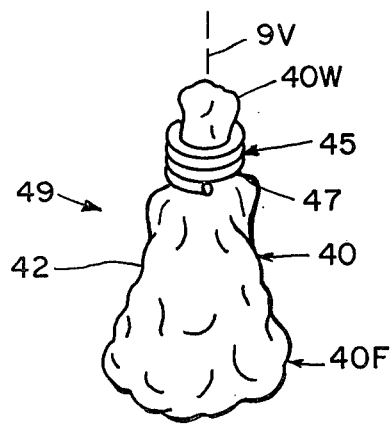
FIG. 4 is a perspective view similar to FIGS. 1 and 3 showing a third embodiment of the present invention.

The third embodiment 49 of FIG. 4 differs from embodiments 9 and 39 in that the bundle 40 comprises a nonoriented mass of coherent randomly disposed hydrophilic fibers. The nodular button 45, which intervenes between wick 40W and flap 40F, comprises hydrophilic fibers identical to those fibers 42 and integrally connected together. 47 indicates the nodular button lower extremity, analagous to lower extremities 17 of embodiments 9 and 39.

Figure 5:
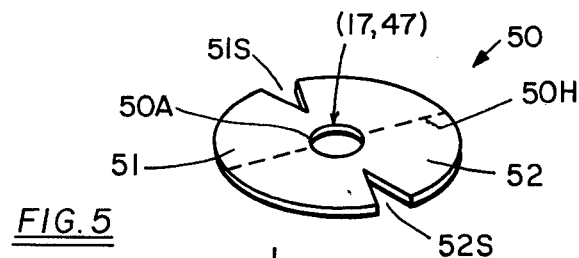
FIG. 5 is a perspective view of a representative flexible skirt member which provides an important further selectable feature for the hygienic articles concept of the present invention.
Figure 6:
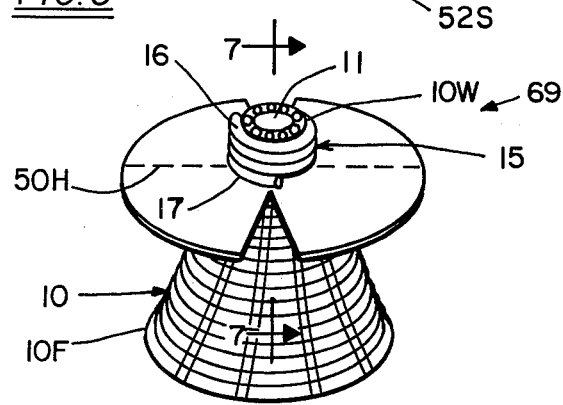
FIG. 6 is a perspective view similar to FIGS. 1, 3, and 4, showing the FIG. 5 skirt member feature incorporated into the hygienic article concept of the present invention.
Figure 7:
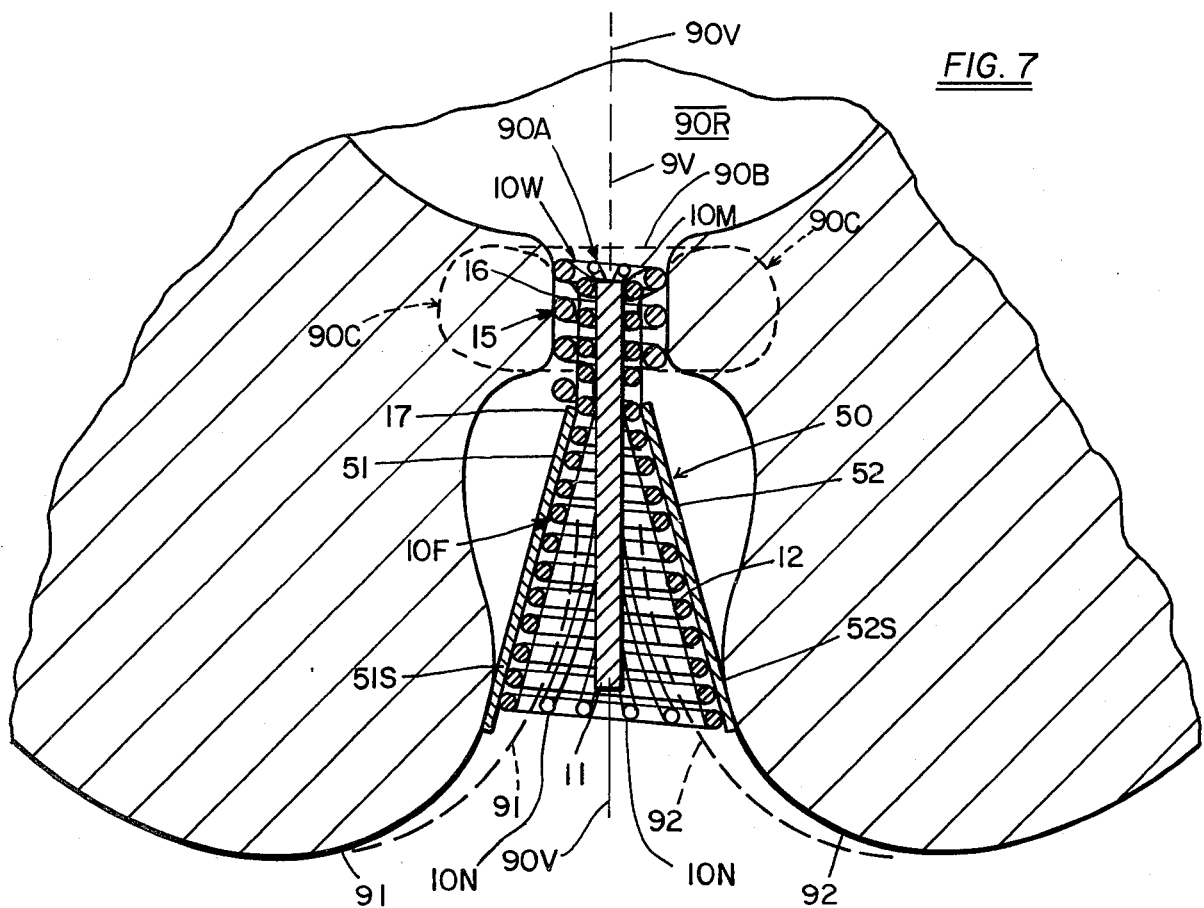
FIG. 7 is a sectional elevational view taken along line 7—7 of the FIG. 6 skirted embodiment and shown removably emplaced at the rectal perineum anatomical region.

FIG. 5 depicts a centrally-apertured (50A) flexible skirt member 50 surrounding a leadward part of the blotter member flap (e.g. immediately below 17, 47). Skirt member 50 is foldable, such as along meridian 50H, so as to conform as two folds 51 and 52 against the respective perineal walls 91 and 92, whereby said skirt folds might augment the functions of the blotter member flap (10F, 30F, 40F) during prolonged periods of sleep or inactivity. In this regard, the skirt member might have a drying or therapeutic agent impregnated therewithin. Skirt member 50 might include at least a pair of colinear radial slits (51S, 52S) to aid the skirt in foldably conforming against the respective perineal walls. FIG. 6 depicts skirt member 50 being anatomically employed with embodiment 9, and surrounding the upper portion of flap 10F. However, it is to be understood that a skirt member might alternatively be similarly employed with embodiments 39 and 49, surrounding the upper portion of the flaps 30F, 40F.

From the foregoing, the construction and operation of the hygienic articles will be readily understood and further explanation is believed to be unnecessary. However, since numerous modifications and changes will readily occur to those skilled in the art, it is not desired to limit the invention to the exact constructions shown and described, and accordingly, all suitable modifications and equivalents may be resorted to, falling within the scope of the appended claims.

What is claimed is as follows:

1. Hygienic article for the rectal perineum region and including a blotter member flap, said article comprising:

A. a bundle of coherent hydrophilic fibers extending longitudinally along a central-axis and having a longitudinal-length from a lead-end to a trail-end, said fibrous bundle longitudinal-length including a relatively shorter leadward wick and a lengthier trailward blotter flap, said wick being positionable terminally within the anus so that the bundle lead-end is within the confines of the anal sphincter muscle to absorb rectal secretia and convey same along the bundle fibers toward the flap and which flap is nestably locatable immediately below the anus so as to conformably abut against the user's perineal walls, said bundle lengthier flap also being at least ten-fold more massive than the bundle shorter wick so as to reduce irritation and promote cleanliness at the perineal walls; and B. a nodular button constrictably surrounding said blotter bundle portion and delineating the juncture of the bundle wick and flap, said nodular button comprising hydrophilic fibers compressed more closely together than are the fibers of said bundle wick and flap, said hygienic article at the nodular button portion being removably emplaceable within the anus and surrounded by the anal sphincter muscle to maintain the article in place and providing a retarder that slows the rectal secretia being conveyed from the bundle wick toward the bundle flap.

2. The hygienic article of claim 1 wherein the blotter member nodular button portion comprises a strand of entwined hydrophilic fibers securely wrapped around the blotter member bundle portion.

3. The hygienic article of claim 2 wherein hydrophilic fibers of the blotter member bundle and nodular button portions are identical type fibers and integrally connected together.

4. The hygienic article of claim 1 wherein at least the bundle trailward blotter flap portion contains therapeutic agent impregnated therewithin.

5. The hygienic article of claim 1 wherein the bundle trailward blotter flap also includes an upwardly convergent wrap surrounding other flap fibers extending along said central-axis, said convergent part also permitting the article to sheath the user's index finger ancillary to removably emplacing same within the anus.

6. The hygienic article of claim 5 wherein the blotter member bundle portion convergent part comprises woven fibers.

7. The hygienic article of claim 1 wherein there is a centrally-apertured flexible skirt member surrounding a leadward part of the bundle member trailward blotter flap, said flexible skirt member (while the article is so removably emplaced) conforming as two folds against the two respective perineal walls whereby said skirt folds might augment blotter functions of the bundle member flap during prolonged periods of sleep or inactivity.

8. The hygienic article of claim 7 wherein the flexible skirt member is of generally circular shape including at least a pair of colinear radial slits to aid the skirt in foldably conforming against the respective perineal walls of the selected user.

9. The hygienic article of claim 8 wherein the flexible skirt is impregnated with a therapeutic agent.

10. The hygienic article of claim 1 wherein the bundle member trailward blotter portion comprises nonwoven fibers oriented in the form of a sheet material which is convolutely wound around said central-axis.

11. The hygienic article of claim 1 wherein the entire blotter member comprises randomly disposed hydrophilic fibers of the cellulosic type and devoid of acidic and alkaline inorganic components.

* * * * *